United States Patent [19]

Krempf et al.

[11] Patent Number: 5,252,309
[45] Date of Patent: Oct. 12, 1993

[54] AZINE SYNTHESIS IN THE ABSENCE OF $CO_2$

[75] Inventors: Gerard Krempf, Lyons; Bertrand Collier, La Barthe de Neste; Pierre Tellier, Lyons; Jean-Pierre Schirmann, Paris, all of France

[73] Assignee: Elf Atochem S.A., Puteaux, France

[21] Appl. No.: 897,830

[22] Filed: Jun. 12, 1992

[30] Foreign Application Priority Data

Jun. 12, 1991 [FR] France .................. 91 07149

[51] Int. Cl.[5] .................. C01B 21/16; C07C 241/00; C07C 241/02
[52] U.S. Cl. ........................ 423/407; 564/249
[58] Field of Search .............. 423/407; 564/249

[56] References Cited

U.S. PATENT DOCUMENTS

| | | |
|---|---|---|
| 3,948,902 | 4/1976 | Schirmann . |
| 4,233,242 | 11/1980 | Nagato et al. .................. 564/249 |
| 4,473,708 | 9/1984 | Kuriyama et al. .................. 564/249 |

FOREIGN PATENT DOCUMENTS

| | | |
|---|---|---|
| 399866 | 11/1990 | European Pat. Off. . |
| 2424890 | 12/1975 | Fed. Rep. of Germany ...... 564/249 |
| 2338252 | 1/1976 | France . |

Primary Examiner—Wayne Langel
Attorney, Agent, or Firm—Burns, Doane, Swecker & Mathis

[57] ABSTRACT

Azines, well suited for hydrolysis into hydrazine, are prepared in high yields by reacting ammonia, aqueous hydrogen peroxide and a carbonyl compound reactant in the presence of a catalytically effective amount of a catalyst medium therefor, i.e., an aqueous solution of ammonium acetate and acetamide or of acetamide and acetic acid, but in the absence of $CO_2$.

15 Claims, 2 Drawing Sheets

AZINE SYNTHESIS IN THE ABSENCE OF CO₂

BACKGROUND OF THE INVENTION

1. Field of the Invention

The present invention relates to the synthesis of azines in reaction zones having a reduced content in $CO_2$.

2. Description of the Prior Art

The synthesis of hydrazine from ammonia and aqueous hydrogen peroxide is described in Ullmann's *Encyclopedia of Industrial Chemistry*, vol. A 13, pages 182-183 (1989).

In a first stage, an azine is formed according to the reaction:

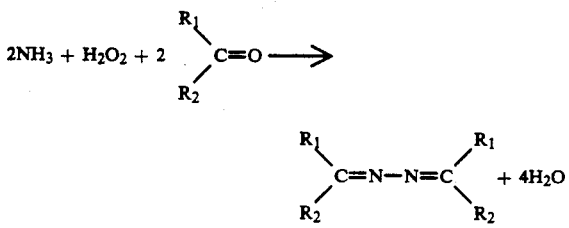

This reaction is carried out in the presence of a catalyst or mixture of catalysts. Such catalyst is employed in the form of a working solution. Upon completion of the reaction, the azine is separated from the working solution.

The working solution is regenerated and then recycled to the first stage. In a second stage, the azine is hydrolyzed to hydrazine and the ketone recovered is also recycled to the first stage:

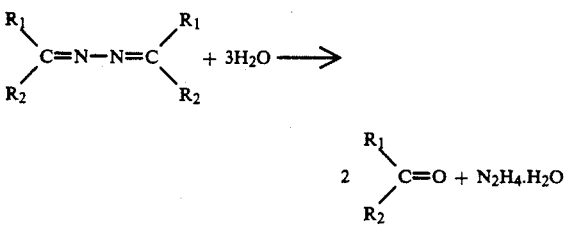

The above process is described, for example, in U.S. Pat. Nos. 3,972,878, 3,972,876, 3,869,541, 3,948,902, 3,956,282, 3,943,152, 4,725,421, 4,093,656, 4,724,133 and in EP-399,866.

In the first stage, the introduction of the reactants $NH_3$ and $H_2O_2$ is carried out.

It has now been found that the presence of $CO_2$ should be avoided to as great an extent as possible during the azine synthesis reaction. For example, when conducting the synthesis of azines by reacting methyl ethyl ketone, $NH_3$ and aqueous hydrogen peroxide in the presence of a working catalyst solution comprising an aqueous solution of acetamide, sodium acetate and disodium phosphate, it was noted that the loss of aqueous hydrogen peroxide by decomposition increased in direct proportion to the $CO_2$ concentration in the reaction mixture, namely, the totality of the working solution plus reactants.

SUMMARY OF THE INVENTION

Accordingly, a major object of the present invention is the provision of an improved process for the synthesis of azines by contacting ammonia, aqueous hydrogen peroxide and a reactant bearing a carbonyl functional group with a working solution containing a catalyst for converting such reactants into an azine, and wherein the process is carried out in the absence of $CO_2$.

DETAILED DESCRIPTION OF THE PREFERRED EMBODIMENTS OF THE INVENTION

Figure 1:
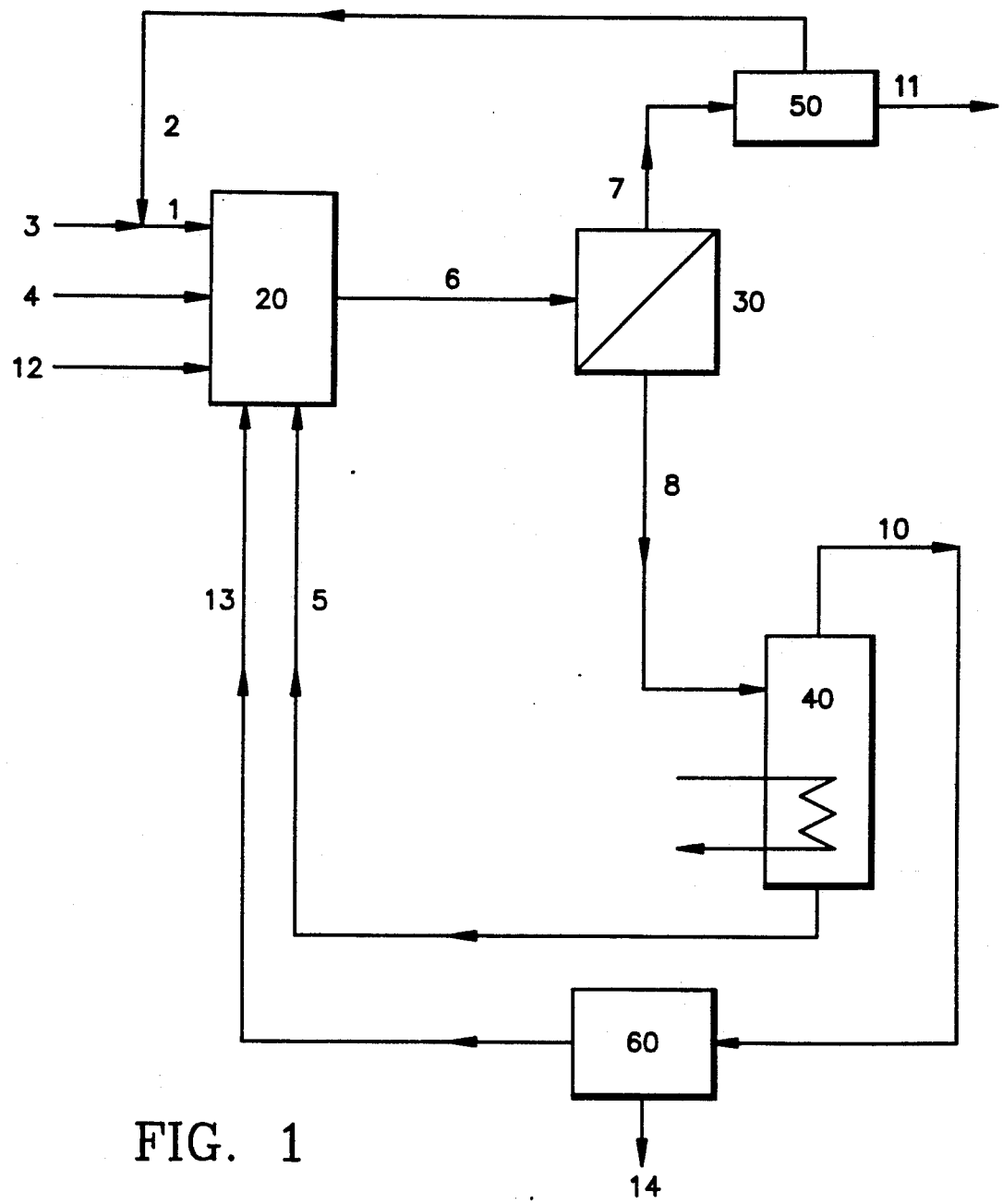
FIG. 1 is a schematic/diagrammatic illustration of one embodiment of the process/apparatus for the synthesis of azines according to the present invention.

More particularly according to the present invention, the basic reaction is per se known to this art and is described in the aforenoted patents. The reactant bearing a carbonyl functional group, or carbonyl compound reactant, is advantageously an aldehyde or a ketone. Acetone, methyl ethyl ketone (MEK), methyl isobutyl ketone or cyclohexanone is suitable in most instances. The working solution may be any solution capable of converting a mixture of ammonia, aqueous hydrogen peroxide and a carbonyl compound reactant into an azine. It is, for example, an aqueous solution of ammonium acetate and acetamide.

By the term "in the absence of $CO_2$" is intended that the operation is carried out with as little $CO_2$ as possible, namely, without introducing $CO_2$ into the reactor, and that the ammonia, the aqueous hydrogen peroxide, the carbonyl compound reactant, the working solution, optionally recycled ammonia and, in general, any feedstream into the reactor, does not contain any $CO_2$. It is possible that $CO_2$ may be formed in the reactor, but the present invention is predicated on the proposition that the inlet feedstreams into the reactor contain little or no $CO_2$. This is all the more unexpected and surprising since, according to FR-2,338,252, if 65 g (3.6 moles) of water, 14.5 g (0.25 moles) of acetone, 5 g (0.1 mole) of aqueous solution of hydrogen peroxide at a concentration of 68% by weight and 0.25 g of the disodium salt of ethylenediaminetetraacetic acid are charged into a reactor and if a stream of $NH_3$ and a stream of $CO_2$ are bubbled therethrough at 25° C., 4.12 g of acetone azine (0.037 moles) are determined in the mixture after 24 hours, which corresponds to a 36.8% yield based on hydrogen peroxide.

The disodium salt of ethylenediaminetetraacetic acid is a sequestrant for heavy ions and thus stabilizes the aqueous hydrogen peroxide.

According to this '252 patent, if the aforesaid example is reproduced without introducing $CO_2$, no trace amounts of azine are determined. $CO_2$ may thus be considered to be a catalyst, since it promotes the production of azine. However, the yield is 36.8% whereas, when a mixture of ammonium acetate, acetamide and disodium phosphate is employed, yields of more than 85% are attained.

The present invention also features a process for the synthesis of azines, in which:

(a) ammonia, aqueous hydrogen peroxide and a carbonyl compound reactant are contacted with a working solution containing a catalyst for converting the reactants into an azine, (b) the azine thus produced is separated from the working solution, (c) the working solution is regenerated by heating it to a temperature of at least 130° C., while removing the water of reaction and the water introduced via the water of dilution of the aqueous hydrogen peroxide in the form of a steam containing water, ammonia, the carbonyl compound reactant and $CO_2$, (d) the working solution is recycled to Stage a, and (e) the outlet stream from Stage c is recycled to the Stage a reaction zone after the $CO_2$ and most of the water have been removed therefrom.

Indeed, it has now been found that, although no $CO_2$ is introduced into the Stage a sequence and although the azine synthesis reaction does not generate $CO_2$, a minor amount of the latter is formed by degradation of the reaction products and reactants under the influence of the aqueous hydrogen peroxide in Stage a and during the regeneration of Stage c. If the $CO_2$ is not purged, a deterioration in the yield of aqueous hydrogen peroxide is observed. In the steam from Stage c, most of the $CO_2$ is in the form of ammonium carbonate.

The ammonia, the reactant bearing a carbonyl functional group which is recovered after the $CO_2$ has synthesis reactor. Example 1 below relates to such a process.

Various techniques may be employed for removing the $CO_2$ and most of the water from the stream emanating from Stage c; this stream can be conveyed to the top of a column with trays or with a packing, which is operated as an exhaustion or stripping column by heating the base thereof such that the ammonia, the carbonyl compound, the $CO_2$ and water are recovered at the top and most of the water at the bottom. The top stream is then condensed and placed under low pressure at a temperature ranging from 20° to 45° C. to retain the $CO_2$ in the form of ammonium carbonate in aqueous solution. The carbonyl compound, the ammonia and the water vapor are then present in the gaseous phase. Advantageously, it suffices to use an absolute pressure ranging from 30 to 120 mm Hg and preferably from 60 to 90 mm Hg absolute.

Figure 2:
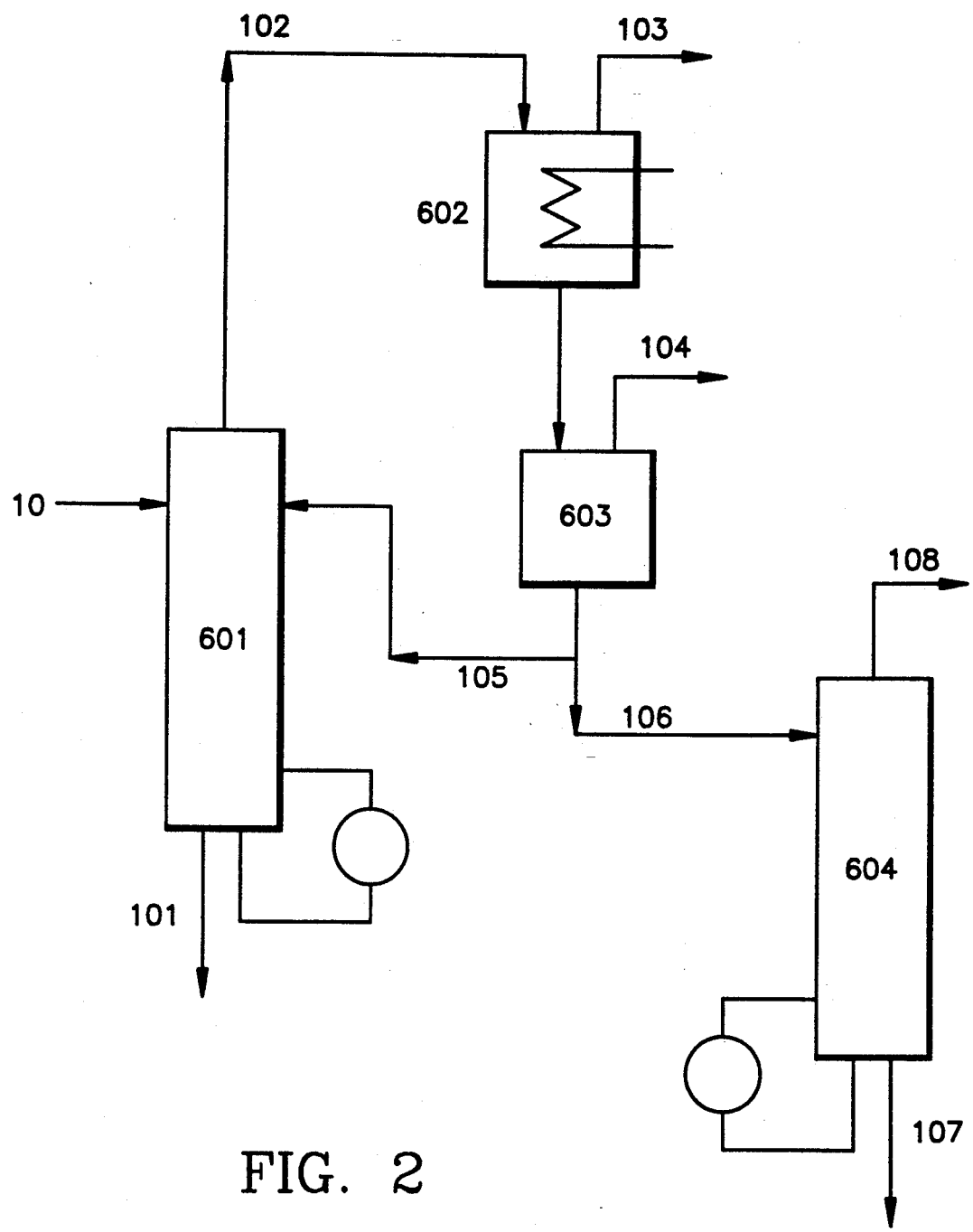
FIG. 2 is a schematic/diagrammatic illustration of another embodiment of the azine synthesis according to the invention.

FIG. 2 describes one embodiment of the invention. The feedstream 10 emanating from Stage c, containing $NH_3$, the reactant bearing a carbonyl functional group, $CO_2$ and water, are introduced into the top of a stripping column 601 fitted with a reboiler. The $CO_2$, in the feedstream 10, is in the form of ammonium carbonate. A stream 101 of water is recovered at the base of the column and a top stream 102 is recovered, which is cooled to a temperature ranging from 30° to 50° C. in a condenser 602. A fraction of the $NH_3$ does not condense and is recycled in a stream 103 to the synthesis reactor of Stage a. The liquid phase is discharged into the trough 603.

Depending on the solubility of the carbonyl compound, there may exist an organic phase which is rich in this reactant and this is recycled via stream 104 to the reactor of Stage a. The aqueous phase present in 603 contains all of the $CO_2$ in the form of ammonium carbonate which was present in the feedstream 10. A fraction 105 constitutes the reflux from the column 601; the stream 106 is flashed at low pressure into a column 604.

The bottom temperature is maintained at from 20° to 45° C. by means of a reboiler, the pressure is maintained at from 60 to 90 mm Hg absolute by means of a vacuum pump or any equivalent device. The bottom stream 107 contains all of the $CO_2$ in the form of ammonium carbonate, water, trace amounts of $NH_3$ and of the carbonyl compound reactant. The top stream 108 contains $NH_3$, the carbonyl compound reactant and water.

In addition to the four products of feedstream 10 indicated above, namely, $NH_3$, the carbonyl compound reactant, the $CO_2$ and the water, there may also be present various organic compounds such as the oxime, azine or secondary butanol. The stream 108 is recycled to the reactor of Stage a.

It is also within the ambit of the invention to remove the $CO_2$ by other means, such as by washing with sodium hydroxide to retain the $CO_2$ in the form of carbonate and to retain the ammonia, the carbonyl compound reactant and the water vapor in gaseous form.

The carbonyl compound reactant is advantageously selected from among the ketones indicated above. MEK is preferably used because MEK azine is insoluble in aqueous solutions, and this facilitates the Stage b sequence. A particularly simple working solution comprises an aqueous solution of acetamide and ammonium acetate, or of acetamide and acetic acid.

In order to further illustrate the present invention and the advantages thereof, the following specific examples are given, it being understood that same are intended only as illustrative and in nowise limitative.

EXAMPLE 1

The procedure of this Example was carried out according to the embodiment of the invention illustrated in FIG. 1 for the synthesis of hydrazine from ammonia and aqueous hydrogen peroxide. The synthesis of the azine was conducted in the reactor 20; inlet 1 indicates the ketone feed, i.e., the recycle emanating from the hydrolysis reactor 50 and an optional topping-off via line 3. Inlet 4 indicates the $NH_3$ feed, inlet 12 the aqueous hydrogen peroxide feed, and line 5 indicates the recycling of the working solution. The product of synthesis is conveyed via conduit 6 into the separator 30, which produces the crude azine at line 7 and the working solution via line 8, the latter also containing ammonia, a minor amount of ketone, the water formed by the reaction and the water which was introduced by the aqueous hydrogen peroxide, since the aqueous hydrogen peroxide is employed at a concentration of not more than 70% by weight in water for reasons of safety.

The separator 30 was a simple phase separator, if the azine was insoluble in the working solution and in the water of reaction; otherwise, a distillation column was employed. The working solution and its regeneration are described in EP-399,866, hereby expressly incorporated by reference. The function of the working solution was to catalyze the synthesis of azines and to entrain the water of reaction and the water introduced with the aqueous hydrogen peroxide via the conduct 8 to the device 40. There the working solution was heated to at least 130° C. and preferably from 150° to 250° C. A stream containing the water formed by the reaction and the water introduced via the aqueous hydrogen peroxide, ammonia and ketone were recovered via line 10 and the regenerated working solution, which was returned to the reactor 20 via line 5. A system for purifying the working solution from its heavy impurities may optionally be arranged along the stream 5; decomposition of the reaction products and of the reactants unavoidably occurred in the reactor 20.

In vessel 50 the azine was hydrolyzed to hydrazine which was drawn off via outlet 11 and via conduit 2 the ketone was recycled to the reactor 20. In a stationary state, the water of dilution of the aqueous hydrogen peroxide, the water formed by the reaction, ammonia and ketone were again present in line 10. The azine synthesis produced 4 moles of water; these 4 moles and the water of dilution of the aqueous hydrogen peroxide were again present in line 10. A fraction of this water was utilized in vessel 50, i.e., 3 moles.

The water balance was in excess, but before purging such water, the ammonia and the ketone which were present were recovered and were returned to the reactor 20. It was not desirable to employ water charged with ammonia for the hydrolysis in vessel 30. In order to exploit the above process economically, it therefore was advantageous to recover the ammonia and the ketone which were present in the stream 10 and recycle same to the reactor 20.

The solution 10 was treated in vessel 60; a steam 14 of purified water and a stream 13 containing water, ammonia and ketone which was recycled to the reactor 20 were obtained. It was determined that, at constant azine output, when such recycling 13 was eliminated, an additional consumption of ammonia and of ketone was noted, corresponding to the amounts which were no longer recycled via line 13, together with an increase in the amount of aqueous hydrogen peroxide required. It thus was found that the stream 13 contained $CO_2$ and that it resulted in an additional requirement for aqueous hydrogen peroxide. Dispensing with the recycling 13 and on injecting $CO_2$ into the reactor 20, additional requirements for aqueous hydrogen peroxide were necessary.

EXAMPLE 2

A synthesis of azines was carried out by reaction of methyl ethyl ketone (MEK), $NH_3$ and aqueous hydrogen peroxide in the presence of a working solution based on acetamide and ammonium acetate; a stream 10 containing MEK, $NH_3$, $CO_2$, $H_2O$, a minor amount of secondary butanol, oxime and azine were obtained in Stage c.

The removal of $CO_2$ and most of the water was conducted according to the embodiment of the invention shown in FIG. 2. The results for two operating velocities are reported in Tables 1 and 2, which follow.

The pressure in column 604 was 90 mm Hg absolute (i.e., 118 mbar), the base temperature of which was 30° C.

TABLE 1

|  | Stream 106 | | Stream 107 | | Stream 108 | |
| --- | --- | --- | --- | --- | --- | --- |
|  | % | kg/h | % | kg/h | % | kg/h |
| $CO_2$ | 1.1 | 6.4 | 1.973 | 6.4 | 0 | 0 |
| $NH_3$ | 18.53 | 107.5 | 9.610 | 31.175 | 29.86 | 76.325 |
| MEK | 17.06 | 99 | 4.273 | 13.86 | 33.308 | 85.14 |
| $BuOH_2$ | 8.88 | 51.5 | 4.531 | 14.7 | 14.396 | 36.8 |
| Azine | 0.62 | 3.6 | 0.709 | 2.3 | 0.508 | 1.3 |
| Oxime | 1.55 | 9.0 | 2.775 | 9 | ca. 0 | ca. 0 |
| Various | 1.38 | 8 | 1.54 | 5 | 1.174 | 3 |
| $H_2O$ | 50.862 | 295 | 74.587 | 241.95 | 20.753 | 53.05 |
| TOTAL | 99.98 | 580 | 99.998 | 324.385 | 99.998 | 255.615 |

TABLE 2

|  | Stream 106 | | Stream 107 | | Stream 108 | |
| --- | --- | --- | --- | --- | --- | --- |
|  | % | kg/h | % | kg/h | % | kg/h |
| $CO_2$ | 0.61 | 1.507 | 1.276 | 1.507 | 0 | 0 |
| $NH_3$ | 19.25 | 47.547 | 4.43 | 5.23 | 32.66 | 42.31 |
| MEK | 22.3 | 55.08 | 4.66 | 5.5 | 38.26 | 49.572 |
| $BuOH_2$ | 2.5 | 6.175 | 1.06 | 1.255 | 3.8 | 4.92 |
| Azine | 0.25 | 0.6175 | 0.33 | 0.3875 | 0.177 | 0.23 |
| Oxime | 1.02 | 2.519 | 1.58 | 1.865 | 0.504 | 0.654 |
| Various | 5.74 | 14.178 | 8.38 | 9.903 | 3.3 | 4.275 |
| $H_2O$ | 48.58 | 120 | 78.26 | 92.4 | 21.3 | 27.6 |

TABLE 2-continued

|  | Stream 106 | | Stream 107 | | Stream 108 | |
| --- | --- | --- | --- | --- | --- | --- |
|  | % | kg/h | % | kg/h | % | kg/h |
| TOTAL | 100 | 247.62 | 99.98 | 118.062 | 100 | 129.56 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an azine in the absence of $CO_2$, comprising reacting ammonia, aqueous hydrogen peroxide and a carbonyl compound reactant in the presence of a catalytically effective amount of a catalyst medium therefor, wherein no $CO_2$ is introduced into the process, and purging $CO_2$ of reaction during the process.

2. The process as defined by claim 1, comprising (a) reacting said ammonia, aqueous hydrogen peroxide and carbonyl compound in the presence of a catalytically effective amount of a liquid catalyst medium therefor, (b) separating the azine thus produced from said liquid catalyst medium, (c) heating said liquid catalyst medium to a temperature of at least 130° C. while removing therefrom water of reaction and water introduced by said aqueous hydrogen peroxide by means of an outlet flowstream which comprises water, ammonia, carbonyl compound reactant and $CO_2$ of reaction, (d) recycling such regenerated liquid catalyst medium to the above Stage (a), and (e) recycling said Stage (c) flowstream to said Stage (a) after removing the $CO_2$ of reaction and the major amount of water therefrom.

3. The process as defined by claim 2, comprising (e) transpiration said flowstream through a stripping column and withdrawing a flowstream which comprises said major amount of water from the base thereof.

4. The process as defined by claim 3, comprising (e) withdrawing an overhead flowstream and placing such flowstream under low pressure at a temperature ranging from 20° to 45° C.

5. The process as defined by claim 4, said low pressure ranging from 30 to 120 mm Hg absolute.

6. The process as defined by claim 1, said carbonyl compound reactant comprising a ketone or aldehyde.

7. The process as defined by claim 6, said carbonyl compound reactant comprising acetone, methyl ethyl ketone, methyl isobutyl ketone or cyclohexanone.

8. The process as defined by claim 6, said catalyst medium comprising an aqueous solution of ammonium acetate and acetamide.

9. The process as defined by claim 4, said Stage (c) regenerated liquid catalyst medium comprising ammonium carbonate.

10. The process as defined by claim 9, said base flowstream comprising ammonium carbonate and said overhead flowstream ammonia, carbonyl compound reactant and water.

11. The process as defined by claim 6, said catalyst medium comprising an aqueous solution of acetamide and acetic acid.

12. The process as defined by claim 1, further comprising hydrolyzing the azine thus produced into hydrazine.

13. The process as defined by claim 10, said carbonyl compound reactant comprising a ketone or aldehyde.

14. The process as defined by claim 2, said carbonyl compound reactant comprising a ketone or aldehyde.

15. The process as defined by claim 2, further comprising hydrolyzing the azine thus produced into hydrazine.

* * * * *